(12) United States Patent
Miyamoto et al.

(10) Patent No.: US 8,303,996 B2
(45) Date of Patent: *Nov. 6, 2012

(54) BARIUM SULFATE-BASED POWDERS AND COSMETICS CONTAINING THE SAME

(75) Inventors: Tsuyoshi Miyamoto, Kanagawa (JP); Katsuki Ogawa, Kanagawa (JP); Sadaki Takata, Kanagawa (JP); Mitsuhiro Denda, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 264 days.

This patent is subject to a terminal disclaimer.

(21) Appl. No.: 10/471,087

(22) PCT Filed: Mar. 7, 2002

(86) PCT No.: PCT/JP02/02122
§ 371 (c)(1),
(2), (4) Date: Feb. 17, 2004

(87) PCT Pub. No.: WO02/072475
PCT Pub. Date: Sep. 19, 2002

(65) Prior Publication Data
US 2004/0126320 A1    Jul. 1, 2004

(30) Foreign Application Priority Data
Mar. 8, 2001    (JP) .................................. 2001-64792

(51) Int. Cl.
*A61K 33/00*    (2006.01)

(52) U.S. Cl. ...................................................... 424/722

(58) Field of Classification Search .................... 424/63, 424/722
See application file for complete search history.

(56) References Cited

U.S. PATENT DOCUMENTS
2,358,050 A * 9/1944 Boulet .......................... 423/554

FOREIGN PATENT DOCUMENTS

| JP | 30-9315 B1 | 12/1955 |
|---|---|---|
| JP | 48-080498 A | 10/1973 |
| JP | 50-033984 B2 | 11/1975 |
| JP | 50-033985 B2 | 11/1975 |
| JP | 52-020660 A | 2/1977 |
| JP | 03-088715 A | 4/1991 |
| JP | 05-058624 A | 3/1993 |
| JP | 05058624 A * | 3/1993 |
| JP | 07-277729 A | 10/1995 |
| JP | 11-035319 A | 2/1999 |

OTHER PUBLICATIONS

Chemical Abstracts 119:31085, Myoshi et al., "Preparation of Barium Sulfate Powder".*

* cited by examiner

*Primary Examiner* — Kevin E Weddington
(74) *Attorney, Agent, or Firm* — Andrew F. Young, Esq.; Lackenbach Siegel, LLP

(57) ABSTRACT

A barium sulfate-based powder is produced by bringing barium ions (A) into contact with sulfate ions (B) in the presence of one or more metallic ion species (C) selected from the group consisting of lithium ions, sodium ions, potassium ions, magnesium ions, calcium ions, zinc ions, and aluminum ions. Thus, barium sulfate-based powders having various characteristics and thus satisfying functional requirements for cosmetics can be obtained.

5 Claims, 4 Drawing Sheets

BARIUM SULFATE-BASED POWDERS AND COSMETICS CONTAINING THE SAME

TECHNICAL FIELD

The present invention relates to inorganic powder which can be incorporated into a cosmetic composition.

BACKGROUND ART

In cosmetic compositions, powders such as barium sulfate are often incorporated for the purpose of imparting covering power or body to the compositions. In particular, in makeup cosmetic compositions such powder serves as an essential component for attaining the purpose.

Characteristics of a cosmetic composition containing powder are greatly affected by components constituting the particles of the powder, as well as by other factors, including the size and shape of the particles. For example, in general, when spherical powder particles are incorporated into a cosmetic composition, the composition tends to exhibit excellent spreadability as compared with a cosmetic composition containing plate-like particles. Meanwhile, when fine powder particles are incorporated into a cosmetic composition, the composition exhibits a fine texture.

At present, demand exists for imparting various functions to cosmetic compositions, and, in order to provide these functions for cosmetic compositions, various attempts have been made to obtain powder particles exhibiting a variety of characteristics; for example, physical or chemical investigations have been performed on processes and conditions for producing powder.

As described above, barium sulfate is generally incorporated as a white extender pigment into a makeup cosmetic composition. In such a case, however, barium sulfate is employed merely as a white pigment and does not impart special functions to the cosmetic composition.

An object to be attained by the present invention is to provide means for imparting various functions to barium sulfate powder so as to meet the aforementioned functional requirements for cosmetic compositions.

DISCLOSURE OF THE INVENTION

In order to achieve the above object, the present inventors have performed extensive studies, and have found that when sulfate ions are brought into contact with barium ions in the presence of various metallic ion species, barium sulfate-based powder exhibiting a variety of characteristics can be produced. The present invention has been accomplished on the basis of this finding.

Accordingly, the present invention provides a process for producing a barium sulfate-based powder (hereinafter the process may be referred to as "the present production process"), which comprises bringing barium ions (A) into contact with sulfate ions (B) in the presence of one or more metallic ion species (C) selected from the group consisting of lithium ions, sodium ions, potassium ions, magnesium ions, calcium ions, zinc ions, and aluminum ions (hereinafter a metallic ion species may be referred to as a "specific metallic ion species"). Also hereinafter, the thus-produced barium sulfate-based powder may be referred to as "the present barium sulfate-based powder."

The present invention also provides a cosmetic composition comprising the present barium sulfate-based powder (hereinafter may be referred to as "the present cosmetic composition").

BEST MODE FOR CARRYING OUT THE INVENTION

Figure 1:
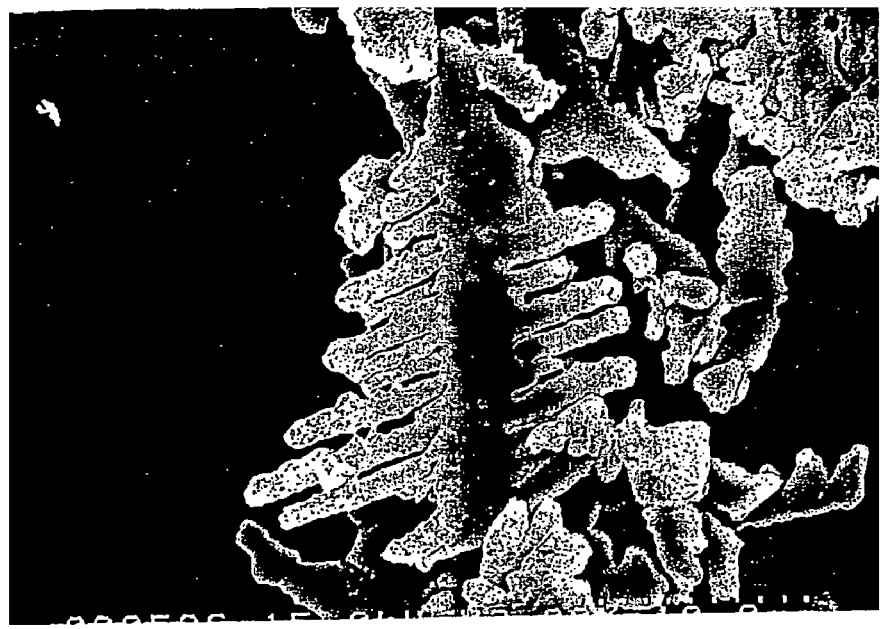
FIG. 1 is an electron micrograph of the present barium sulfate-based powder produced in the presence of zinc ions (magnification: ×3,000)

Embodiments of the present invention will next be described.

1. The Present Production Process and the Present Barium Sulfate-Based Powder

In the present production process, generally, barium ions and sulfate ions are brought into contact with a specific metallic ion species in a solvent which can dissolve solutes capable of dissociating these ions and ion species. No particular limitations are imposed on the solvent to be employed, so long as it can dissolve solutes to be employed, thereby dissociating ions of interest. Examples of the solvent include water, methyl alcohol, ethyl alcohol, butyl alcohol, propyl alcohol, and isopropyl alcohol.

Examples of solutes which can dissociate barium ions [component (A) in the present invention] in a solvent include barium compounds such as barium hydroxide, barium chloride, barium sulfide, barium nitrate, and barium acetate (hereinafter a solution in which a barium compound is dissolved may be referred to as a "barium solution"). Of these compounds, barium chloride and barium hydroxide are preferred, because disposal of by-products produced during the course of reaction can be performed with ease.

Example of solutes which can dissociate sulfate ions [component (B) in the present invention] in a solvent include sulfate compounds such as sulfuric acid, sodium sulfate, sodium hydrogensulfate, ammonium sulfate, potassium sulfate, and lithium sulfate (hereinafter a solution in which a sulfate compound is dissolved may be referred to as a "sulfate solution"). Of these compounds, sulfuric acid, sodium sulfate, and ammonium sulfate are preferred, because disposal of by-products produced during the course of reaction can be performed with ease.

The concentration of a barium compound in a barium solution and the concentration of a sulfate compound in a sulfate solution—the barium compound and the sulfate compound being employed in the production process for the present barium sulfate-based powder—are typically 0.01 mmol/L to 1 mol/L, preferably 1 to 100 mmol/L. When the concentration is less than 0.01 mmol/L, industrial production efficiency of the present barium sulfate-based powder tends to be lowered. In contrast, when the concentration exceeds 1 mol/L, the supersaturation degree of a substance dissolved in the solution increases, generating large amounts of particle nuclei. As a result, large amounts of fine barium sulfate particles are generated and the particles forms aggregation. Therefore, the present barium sulfate-based powder (the final product) tends to impair the favorable property for a cosmetic composition.

Examples of solutes which can dissociate specific metallic ion species [component (C) in the present invention] (specifically, lithium ions, sodium ions, potassium ions, magnesium ions, calcium ions, zinc ions, and aluminum ions) include salts of these specific metallic ion species. Specific examples include lithium salts such as lithium hydroxide, lithium chloride, lithium nitrate, lithium carbonate, and lithium acetate; sodium salts such as sodium hydroxide, sodium chloride, sodium nitrate, sodium carbonate, and sodium acetate; potassium salts such as potassium hydroxide, potassium chloride, potassium nitrate, potassium carbonate, and potassium acetate; magnesium salts such as magnesium hydroxide, magnesium chloride, magnesium nitrate, magnesium carbonate, and magnesium acetate; calcium salts such as calcium hydroxide, calcium chloride, calcium nitrate, calcium carbonate, and calcium acetate; zinc salts such as zinc hydroxide, zinc chloride, zinc nitrate, zinc carbonate, and zinc acetate; and aluminum salts such as aluminum hydroxide, aluminum chloride, aluminum nitrate, aluminum carbonate, and aluminum acetate (hereinafter a solution in which a salt of a specific metallic ion species is dissolved may be referred to as a "specific metallic ion solution").

In the present invention, a barium sulfate-based powder of interest can also be produced through combined use of an organic anion species and a specific metallic ion species. In this case, an organic anion species capable of forming a complex with barium ions is preferred. For example, acetic acid, EDTA, or NTA may be employed for providing such an organic anion species.

In the present production process, specific metallic ion species may be employed singly or in combination of two or more species. Therefore, if desired, one or more of the aforementioned salts of specific metallic ion species may be employed for production of the present barium sulfate-based powder.

When the present production process is performed, preferably, a specific metallic ion species is caused to coexist with barium ions and sulfate ions such that the amount of the specific metallic ion species falls within a range of 0.001 to 10 equivalents on the basis of 1 equivalent of the barium ions. When the amount of the specific metallic ion species is less than 0.001 equivalents on the basis of 1 equivalent of the barium ions, difficulty may be encountered in sufficiently obtaining effects from coexistence between the barium ions and the specific metallic ion species. In contrast, when the amount of the specific metallic ion species exceeds 10 equivalents on the basis of 1 equivalent of the barium ions, aggregation of the resultant barium sulfate-based powder occurs. When the thus-aggregated powder is incorporated into a cosmetic composition, characteristics of the composition, such as sensation upon use, tend to be impaired. Therefore, preferably, a specific metallic ion solution to be employed in the present production process is prepared such that the amount of the specific metallic ion species in the solution falls within the aforementioned range.

A first specific embodiment of the present production process is drawn to a process in which barium ions (A) are brought into contact with a specific metallic ion species (C), and subsequently sulfate ions (B) are brought into contact with the resultant mixture, to thereby yield the present barium sulfate-based powder (hereinafter the process may be referred to as "the first production process").

Specifically, the first production process can be performed by mixing together a barium solution and a specific metallic ion solution, and then adding a sulfate solution to the resultant mixture.

A second specific embodiment of the present production process is drawn to a process in which three components; i.e., barium ions (A), sulfate ions (B), and a specific metallic ion species (C), are brought into contact with one another substantially simultaneously, to thereby yield the present barium sulfate-based powder (hereinafter the process may be referred to as "the second production process").

Specifically, the second production process can be performed by bringing a barium solution, a sulfate solution, and a specific metallic ion solution into contact with one another substantially simultaneously (generally, adding the barium solution and the sulfate solution to the specific metallic ion solution).

In each of the first and second production processes, preferably, the reaction temperature is 50 to 100° C., more preferably 70 to 100° C. Also, in both production processes, the ratio by mol of sulfate ions to barium ions is preferably determined to be 1:2 to 2:1.

After the aforementioned production process is performed, additional steps required for producing the present barium sulfate-based powder, including a step for removing by-products and a crushing step, may be carried out by means of customary techniques.

Thus, the present barium sulfate-based powder can be produced.

In the production process for the present barium sulfate-based powder, a specific metallic ion species, which is brought into contact with barium ions and sulfate ions, can be appropriately chosen and reaction conditions can be appropriately regulated for predetermining the shape, size, and color of particles of the powder, whereby a powder of self-organized particles can be obtained. Thus, it is possible to produce functionalized barium sulfate-based powders having different characteristics in terms of adhesion, gloss, light scattering, and apparent specific gravity (the presence/absence of "soft" feel). The thus-produced barium sulfate-based powder is particularly suitable for use in a cosmetic composition.

The present barium sulfate-based powder may further be subjected to, for example, a known water repellent treatment. Examples of water repellents include silicone oil, fatty acid metallic salts, alkylphosphoric acids, alkali metal salts or amine salts of alkylphosphoric acids, and N-mono(long-chain aliphatic acyl) basic amino acids.

2. The Present Cosmetic Composition

No particular limitations are imposed on the amount of the present barium sulfate-based powder to be incorporated into the present cosmetic composition, and the incorporation amount may be arbitrarily determined in accordance with, for example, specific characteristics of the powder that are determined by a specific metallic ion species employed in the present production process or by other conditions, with the physical form of the cosmetic composition, and with the purpose of incorporation. The incorporation amount is typically 1 to 60 mass %, preferably about 5 to about 35 mass %, on the basis of the entirety of the cosmetic composition.

As in the case of conventional barium sulfate powder, the present barium sulfate-based powder may be incorporated as a white extender pigment into a cosmetic composition. The purpose of incorporation of the present barium sulfate-based powder varies in accordance with specific characteristics of the powder.

Since the present cosmetic composition contains the present barium sulfate-based powder, the composition is endowed with specific characteristic features in terms of, for example, sensation upon use, covering property, and aesthetic property.

So long as effects of the invention are not impaired, if desired, the present cosmetic composition may contain, in addition to the present barium sulfate-based powder serving as an essential component, components which are generally incorporated into cosmetic compositions; for example, oil components, surfactants, powdery components other than the present barium sulfate-based powder, water-soluble polymers, preservatives, various pharmaceutically active components, dyes, perfumes, humectants, ultraviolet absorbers, inorganic salts or organic salts, chelating agents, pH modifiers, water, and lower alcohols.

No particular limitations are imposed on the physical form or the product form of the present cosmetic composition. However, the present cosmetic composition generally assumes the form of a makeup cosmetic composition, in consideration of the inherent nature of the present barium sulfate-based powder. Specific examples of the product form of the makeup cosmetic composition include, but are not limited to, a liquid foundation, a cream foundation, an oily solid cosmetic product, a lipstick, a powdery foundation, a cosmetic powder, a compacted cosmetic powder, an eye-shadow, a face powder, a cheek rouge, an eyeliner, and an eyebrow pencil. If desired, the present barium sulfate-based powder may be incorporated into various other makeup base cosmetics.

EXAMPLES

The present invention will next be described in more detail by way of Examples, which should not be construed as limiting the invention thereto.

Production Example

A 60 mmol/L aqueous barium chloride solution (500 mL), a 60 mmol/L aqueous zinc chloride solution (500 mL), and ion exchange water (1,000 mL) were added to a round-bottom separable flask (capacity: 3,000 mL), and then mixed together under stirring. The resultant liquid mixture was heated to 100° C., and a 60 mmol/L aqueous sodium sulfate solution (500 mL) was added dropwise thereto under stirring. Simultaneous with dropwise addition of the aqueous sodium sulfate solution, white barium sulfate was generated and precipitated, and as a result, the reaction mixture assumed a suspension. Following completion of addition of the aqueous sodium sulfate solution, reaction was allowed to proceed for one hour. After completion of reaction, the resultant reaction mixture was cooled to room temperature. The thus-obtained solid product was allowed to settle, followed by filtration and then washing with water, to thereby remove salts. Subsequently, the product was dried at 120° C. for 12 hours. The resultant solid product was then subjected to crushing treatment (5-minute crushing treatment by use of a small-sized crushing apparatus), to thereby yield a white powder (Production Example 1).

Subsequently, the procedure of the above Production Example was repeated, except that the concentration of the aqueous barium chloride solution, the concentration of the aqueous sodium sulfate solution, the coexisting salt species, and the concentration of the aqueous coexisting salt solution were changed as shown in Table 1, to thereby produce the present barium sulfate-based powder.

In Comparative Production Example, the procedure of Production Example 1 was repeated, except that a coexisting aqueous salt solution was not added, and the amount of ion exchange water was changed to 1,500 mL, to thereby produce a white powder.

TABLE 1

| Production Example | Concentration of aqueous barium chloride solution (mmol/L) | Concentration of aqueous sodium sulfate solution (mmol/L) | Coexisting salt | Concentration of aqueous coexisting salt solution (mmol/L) |
|---|---|---|---|---|
| 1 | 60 | 60 | Zinc chloride | 60 |
| 2 | 60 | 60 | Zinc chloride | 6 |
| 3 | 60 | 60 | Zinc chloride | 0.6 |
| 4 | 6 | 6 | Zinc chloride | 6 |
| 5 | 600 | 600 | Zinc chloride | 6 |
| 6 | 60 | 80 | Zinc chloride | 6 |
| 7 | 60 | 40 | Zinc chloride | 6 |
| 8 | 60 | 60 | Lithium chloride | 60 |
| 9 | 60 | 60 | Sodium chloride | 60 |
| 10 | 60 | 60 | Potassium chloride | 60 |
| 11 | 60 | 60 | Magnesium chloride | 60 |
| 12 | 60 | 60 | Calcium chloride | 60 |
| 13 | 60 | 60 | Aluminum chloride | 60 |

Subsequently, each of the barium sulfate-based powders produced in the aforementioned Production Examples and Comparative Production Example was evaluated through (1) observation of particle structure and measurement of particle size, (2) assessment of optical performance, and (3) actual use tests of a cosmetic composition containing the powder.

(1) Observation of Particle Structure and Measurement of Particle Size

Figure 2:
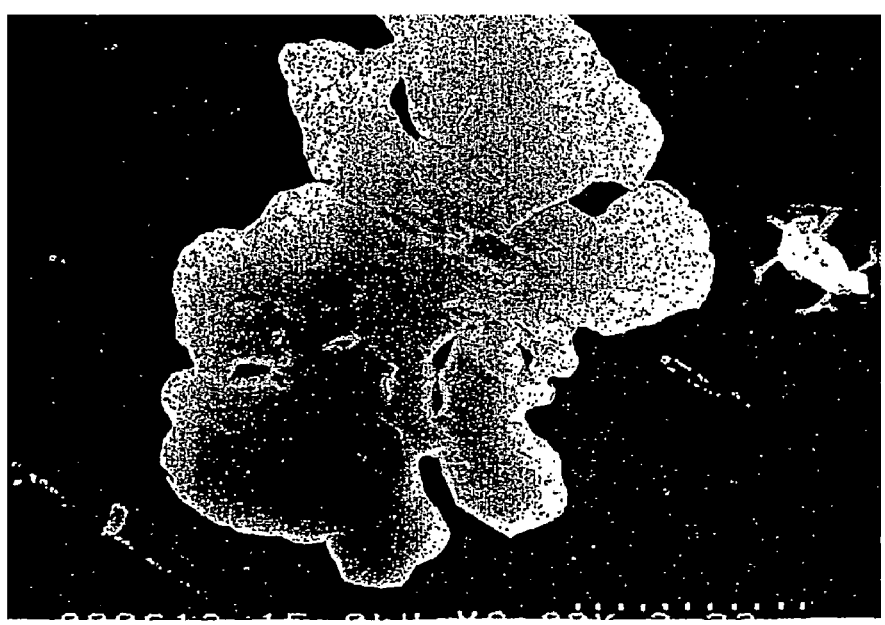
FIG. 2 is an electron micrograph of the present barium sulfate-based powder produced in the presence of lithium ions (magnification: ×9,000)
Figure 3:
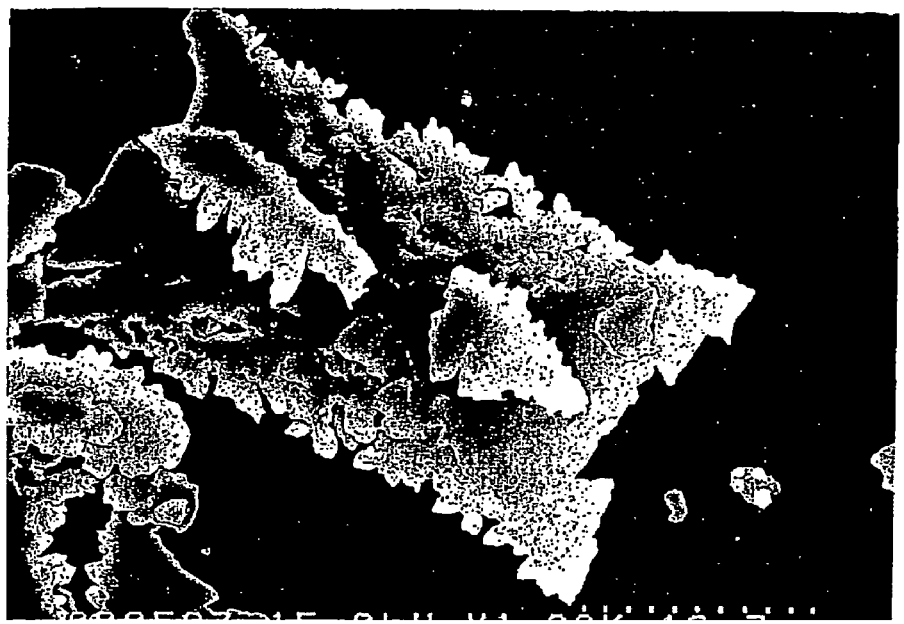
FIG. 3 is an electron micrograph of the present barium sulfate-based powder produced in the presence of sodium ions (magnification: ×1,800)
Figure 4:
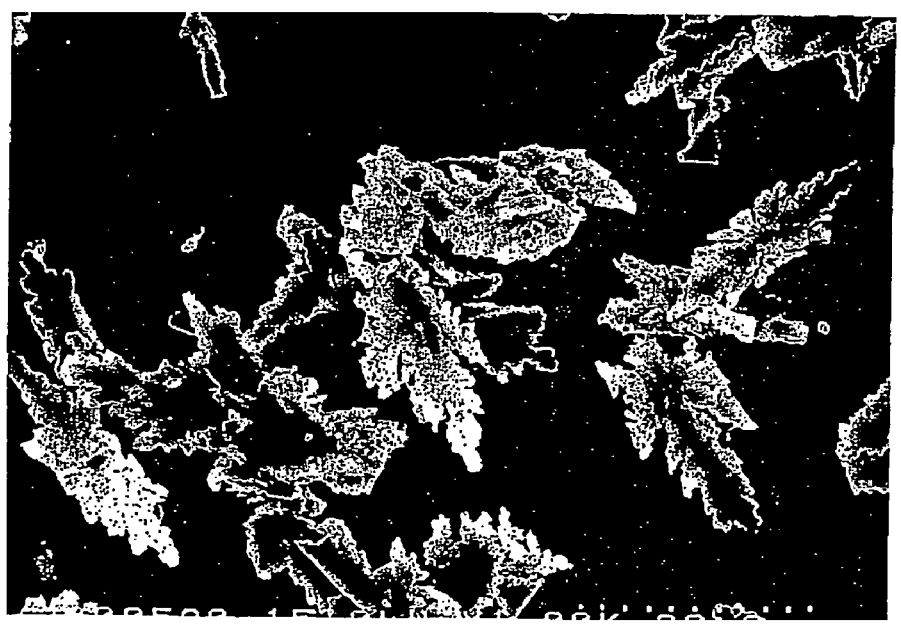
FIG. 4 is an electron micrograph of the present barium sulfate-based powder produced in the presence of potassium ions (magnification: ×1,000)
Figure 5:
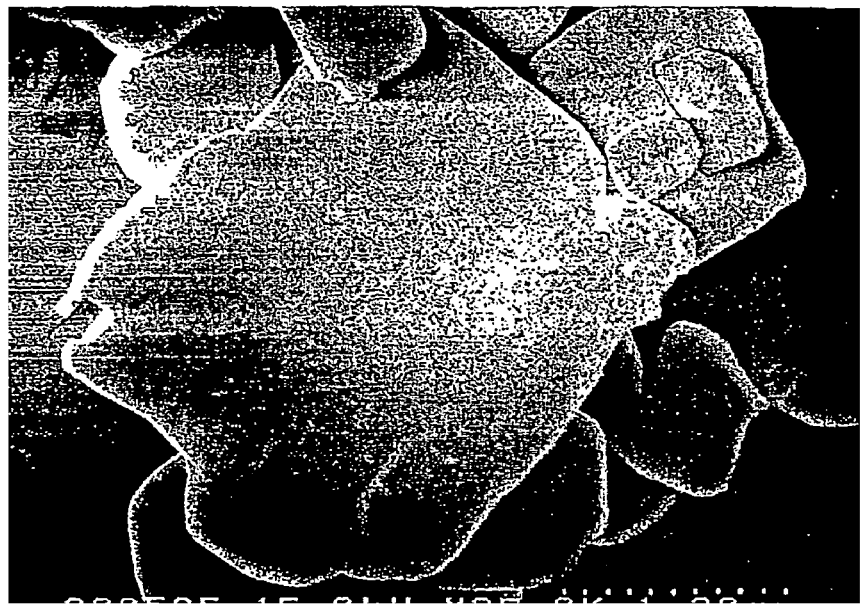
FIG. 5 is an electron micrograph of the present barium sulfate-based powder produced in the presence of magnesium ions (magnification: ×25,000)
Figure 6:
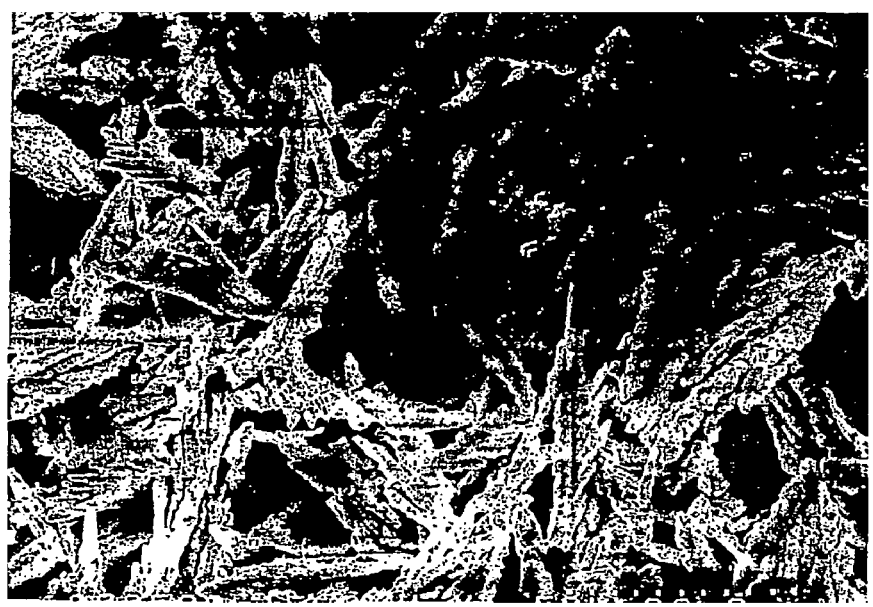
FIG. 6 is an electron micrograph of the present barium sulfate-based powder produced in the presence of calcium ions (magnification: ×1,500)
Figure 7:
FIG. 7 is an electron micrograph of the present barium sulfate-based powder produced in the presence of aluminum ions (magnification: ×6,000)
Figure 8:
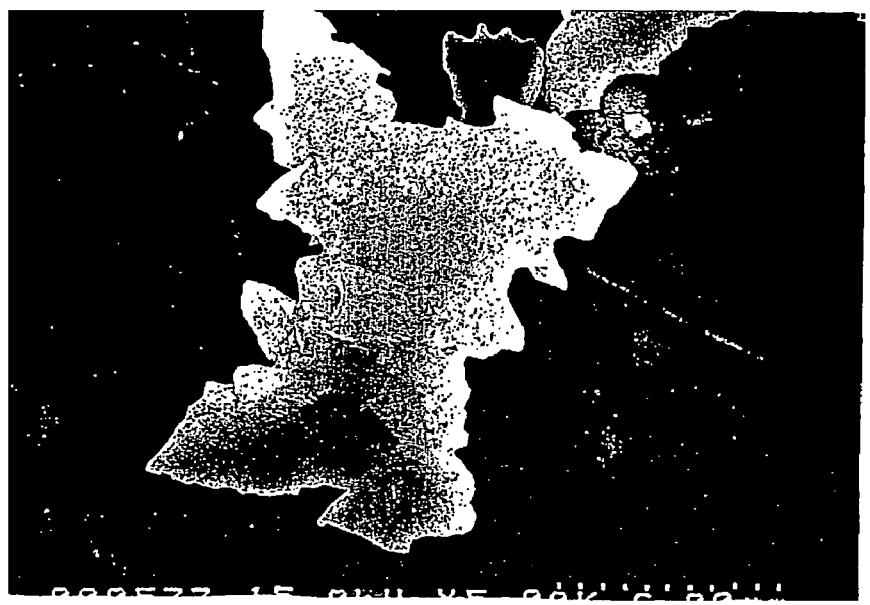
FIG. 8 is an electron micrograph of barium sulfate-based powder produced in the absence of a specific metallic ion species (magnification: ×5,000).

Each sample of the aforementioned barium sulfate-based powders was observed under an electron microscope (S4500, product of Hitachi Ltd.) at a magnification of ×1,000 to ×25,000, to thereby identify the structure of particles of the powder sample. In addition, the length of the major axis of an arbitrarily selected particle of the powder that has an average particle size was measured. FIGS. 1 through 8 show electron micrographs of the barium sulfate-based powders of some of the Production Examples.

(2) Evaluation of Optical Performance

A double-sided tape (product of Sumitomo 3M Ltd.) was attached to a black paper sheet, and the barium sulfate-based powder was applied uniformly to the surface of an adhesive layer by use of a makeup brush, to thereby prepare a test piece (in this case, particles of the powder were not aligned regularly, but were affixed to the adhesive layer at random orientations). Subsequently, the test piece was unidirectionally irradiated with white light, and the thus-irradiated test piece was visually observed. The optical performance of the barium sulfate-based powder was evaluated on the basis of the following criteria.

<Evaluation Criteria> i) When the powder has surface gloss, evaluation "gloss" is given.

ii) When the test piece is inclined with respect to a light source, and the degree of change in gloss is low, the powder is evaluated as having diffusion ability, and evaluation "highly diffusible" or "diffusible" is given.

iii) When particles of the powder uniformly adhere to the adhesive layer and surface roughness is not observed on a layer of the particles, the powder is evaluated as having matte texture, and evaluation "matte" is given.

(3) Evaluation by Means of Actual Use Tests of a Cosmetic Composition Containing the Powder.

Makeup cosmetic compositions having the following formulations and containing the barium sulfate-based powders were prepared through a customary method, and the thus-prepared compositions were evaluated in terms of sensation upon use by means of actual use tests.

(Formulations)

Example 1

Powdery Foundation

| Components | Amount (mass %) |
| --- | --- |
| Seripearl (Sericite) | 17 |
| Synthetic mica | 10 |
| Talc | Balance |
| The barium sulfate-based power of Production Example 1 | 18 |
| Red iron oxide | 0.8 |
| Yellow iron oxide | 2 |
| Black iron oxide | 0.1 |
| Silicone elastic powder | 1 |
| Spherical polyethylene | 4 |
| Dimethylpolysiloxane | 3 |
| Liquid paraffin | 5 |
| Vaseline | 5 |
| Sorbitan sesquiisostearate | 1 |
| Paraben | Suitable amount |
| Antioxidant | Suitable amount |
| Perfume | Suitable amount |

Comparative Example 1

A powdery foundation containing butterfly-shaped barium sulfate powder (barium sulfate powder of Example 1 described in Japanese Patent Application Laid-Open (kokai) No. 7-296123) (18 mass %) in place of the barium sulfate-based powder of Production Example 1 employed in Example 1.

Comparative Example 2

A powdery foundation containing plate-like barium sulfate powder (plate-like barium sulfate H: product of Sakai Chemical Industry Co., Ltd.) (18 mass %) in place of the barium sulfate-based powder of Production Example 1 employed in Example 1.

Comparative Example 3

A powdery foundation containing plate-like barium sulfate powder (plate-like barium sulfate HL: product of Sakai Chemical Industry Co., Ltd.) (18 mass %) in place of the barium sulfate-based powder of Production Example 1 employed in Example 1.

Example 2

Powdery Foundation for Summer Use (Powdery Solid Foundation for Summer Use Which can Also be Used With Water)

| Components | Amount (mass %) |
| --- | --- |
| Silicone-treated sericite | 18 |
| Silicone-treated mica | Balance |
| Silicone-treated talc | 15 |
| The barium sulfate-based power of Production Example 1 (treated with silicone) | 12 |
| Fine particulate titanium oxide treated with aluminum stearate | 6 |
| Silicone-treated red iron oxide | 1.2 |
| Silicone-treated yellow iron oxide | 2.5 |
| Silicone-treated black iron oxide | 0.9 |
| Polyurethane powder | 6 |
| Paraben | Suitable amount |
| Dimethylpolysiloxane | 4 |
| Methylphenylpolysiloxane | 3 |
| Octyl methoxycinnamate | 3 |
| Polyether silicone | 2 |
| Antioxidant | Suitable amount |
| Perfume | Suitable amount |

Example 3

Powdery Foundation for Summer Use

A powdery foundation for summer use containing the barium sulfate-based powder of Production Example 11 (treated with silicone) (12 mass %) in place of the barium sulfate-based powder of Production Example 1 (treated with silicone) employed in Example 2.

Example 4

Powdery Foundation for Summer Use

A powdery foundation for summer use containing the barium sulfate-based powder of Production Example 9 (treated with silicone) (12 mass %) in place of the barium sulfate-based powder of Production Example 1 (treated with silicone) employed in Example 2.

Comparative Example 4

A powdery foundation for summer use containing barium sulfate BF-1 (product of Sakai Chemical Industry Co., Ltd.)

(12 mass %) in place of the barium sulfate-based powder of Production Example 1 (treated with silicone) employed in Example 2.

Example 5

Face Powder

| Components | Amount (mass %) |
|---|---|
| Talc | Balance |
| Mica | 25 |
| The barium sulfate-based power of Production Example 1 | 35 |
| Fine particulate titanium oxide | 3 |
| Spherical silicone powder | 8 |
| Vaseline | 1 |
| Squalane | 3 |
| Ester oil | 1 |
| Paraben | Suitable amount |
| Antioxidant | Suitable amount |
| Perfume | Suitable amount |

Comparative Example 5

A face powder containing plate-like barium sulfate H (product of Sakai Chemical Industry Co., Ltd.) (35 mass %) in place of the barium sulfate-based powder of Production Example 1 employed in Example 5.

Comparative Example 6

A face powder containing plate-like barium sulfate HM (product of Sakai Chemical Industry Co., Ltd.) (35 mass %) in place of the barium sulfate-based powder of Production Example 1 employed in Example 5.

Example 6

W/O-Type Emulsified Cream Foundation

| Components | Amount (mass %) |
|---|---|
| Talc | 8 |
| Sericite | 7 |
| The barium sulfate-based powder of Production Example 1 | 15 |
| Red iron oxide | 0.3 |
| Yellow iron oxide | 1.2 |
| Black iron oxide | 0.6 |
| Spherical polyethylene powder | 6 |
| Squalane | 10 |
| Olive oil | 10 |
| Stearic acid | 2 |
| Glyceryl monostearate | 2 |
| POE (40) sorbitan monostearate | 2 |
| Glycerin | 5 |
| Triethanolamine | 0.8 |
| pH modifier | Suitable amount |
| Preservative | Suitable amount |
| Ion exchange water | Balance |

Example 7

W/O-Type Emulsified Cream Foundation

A W/O-type emulsified cream foundation containing the barium sulfate-based powder of Production Example 11 (15 mass %) in place of the barium sulfate-based powder of Production Example 1 employed in Example 6.

Test Method

The above-prepared cosmetic compositions were applied to the faces of 20 female panelists, and the compositions were evaluated in terms of the following items: effect of covering differences in skin color (e.g., dull skin appearance, spots, and freckles), appropriate gloss attained in finish of makeup, natural appearance, and clearness. Evaluation was performed on the basis of the following criteria.

<Evaluation Criteria>

17 or more panelists evaluated "good": AA 12 to 16 panelists evaluated "good": BB 9 to 11 panelists evaluated "good": CC 5 to 8 panelists evaluated "good": DD 4 or fewer panelists evaluated "good": EE (a) Table 2 shows the results of the aforementioned evaluations (1) and (2).

TABLE 2

| Production Examples | Structure | Particle size (μm) | Optical performance |
|---|---|---|---|
| Production Example 1 | Acicular large branched structure (FIG. 1) | 20 to 30 | Diffusible |
| Production Example 8 | Plate-like structure (FIG. 2) | 5 to 20 | Diffusible |
| Production Example 9 | Rectangular plate-like layered structure (FIG. 3) | 30 to 50 | Diffusible |
| Production Example 10 | Acicular branched structure (FIG. 4) | 20 to 30 | Highly diffusible |
| Production Example 11 | Planar plate-like structure (FIG. 5) | <5 | Matte |
| Production Example 12 | Acicular small branched structure (FIG. 6) | 20 to 30 | Diffusible |
| Production Example 13 | Planar plate-like structure (FIG. 7) | 5 to 10 | Matte |
| Comparative Production Example 1 | Plate-like structure (FIG. 8) | 10 to 20 | Gloss |

As is clear from Table 2, when various specific metallic ion species are caused to coexist with barium ions and sulfate ions in the production process for barium sulfate-based powder, barium sulfate-based powders of different structures and optical performances are produced.

(b) Tables 3 through 6 show the results of the actual use tests (3).

TABLE 3

| Ex. No. | Covering effect | Gloss | Natural appearance | Clearness |
|---|---|---|---|---|
| Example 1 | AA | BB | AA | AA |
| Comparative Example 1 | CC | DD | CC | BB |
| Comparative Example 2 | BB | CC | BB | BB |
| Comparative Example 3 | CC | DD | CC | BB |

The evaluation results show that when the present barium sulfate-based powder of Production Example 1 is incorporated into a makeup cosmetic composition, the composition provides intended benefits upon use.

TABLE 4

| Ex. No. | Covering effect | Gloss | Natural appearance | Clearness |
|---|---|---|---|---|
| Example 2 | AA | AA | BB | BB |
| Example 3 | AA | AA | AA | BB |
| Example 4 | BB | AA | AA | BB |
| Comparative Example 4 | CC | DD | DD | CC |

The evaluation results show that when the present barium sulfate-based powder of Production Example 1, 9, or 11 (treated with silicone) is incorporated into a makeup cosmetic composition, the composition provides intended benefits upon use.

TABLE 5

| Ex. No. | Covering effect | Gloss | Natural appearance | Clearness |
|---|---|---|---|---|
| Example 5 | AA | AA | AA | BB |
| Comparative Example 5 | CC | CC | BB | CC |
| Comparative Example 6 | CC | BB | BB | CC |

The evaluation results show that when the present barium sulfate-based powder of Production Example 1 is incorporated into a makeup cosmetic composition, the composition provides intended benefits upon use.

TABLE 6

| Ex. No. | Covering effect | Gloss | Natural appearance | Clearness |
|---|---|---|---|---|
| Example 6 | AA | AA | AA | BB |
| Example 7 | AA | AA | AA | BB |

The evaluation results show that when the present barium sulfate-based powder of Production Example 1 or 11 is incorporated into a makeup cosmetic composition, even if the composition is emulsified, the composition provides intended benefits upon use.

Industrial Applicability

The present invention provides means for imparting various functions to barium sulfate powder.

The invention claimed is:

1. A process for producing a barium sulfate-based powder, which comprises:
   bringing barium chloride into contact with sodium chloride so as to form a resultant mixture thereof, wherein sodium chloride coexists with barium chloride in the resultant mixture such that the amount of sodium chloride falls within a range of 0.001 to 10 equivalents of chloride ion of sodium chloride on the basis of 1 equivalent of barium ion of barioum chloride;
   and subsequently
   bringing sodium sulfate into contact with the resultant mixture.

2. A barium sulfate-based powder produced by the process of claim 1.

3. The process for producing a barium sulfate-based powder according to claim 1, wherein the ratio by mol of sulfate ion of sodium sulfate to barium ion of barium chloride is 1:2 to 2:1.

4. The process for producing a barium sufate-based powder according to claim 1, wherein an aqueous solution of barium chloride is brought into contact with an aqueous solution of sodium sulfate in the presence of an aqueous solution of sodium chloride.

5. The process for producing barium sulfate-based powder according to claim 1, wherein the barium sulfate-based powder consists essentially of barium sulfate.

* * * * *